(12) United States Patent
Konagai et al.

(10) Patent No.: US 9,476,799 B2
(45) Date of Patent: Oct. 25, 2016

(54) METHOD AND APPARATUS FOR MEASURING CORROSION OF MOBILE BODY

(71) Applicants: SUZUKI MOTOR CORPORATION, Shizuoka-Ken (JP); JFE STEEL CORPORATION, Tokyo (JP)

(72) Inventors: Nobutoshi Konagai, Shizuoka-Ken (JP); Ruri Nakada, Shizuoka-Ken (JP); Kouta Sako, Shizuoka-Ken (JP); Yuya Ito, Shizuoka-Ken (JP); Sachiko Suzuki, Tokyo (JP); Satoru Ando, Tokyo (JP); Yoshiharu Sugimoto, Tokyo (JP)

(73) Assignees: SUZUKI MOTOR CORPORATION, Shizuoka-Ken (JP); JFE STEEL CORPORATION, Tokyo (JP)

( * ) Notice: Subject to any disclaimer, the term of this patent is extended or adjusted under 35 U.S.C. 154(b) by 725 days.

(21) Appl. No.: 13/912,534

(22) Filed: Jun. 7, 2013

(65) Prior Publication Data

US 2013/0332087 A1    Dec. 12, 2013

(30) Foreign Application Priority Data

Jun. 8, 2012    (JP) ................. 2012-130534

(51) Int. Cl.
*G01B 3/44* (2006.01)
*G01B 3/00* (2006.01)
*G01B 5/28* (2006.01)
*G01M 17/00* (2006.01)
*G01M 3/16* (2006.01)
*G01M 17/007* (2006.01)

(52) U.S. Cl.
CPC .............. *G01M 17/00* (2013.01); *G01M 3/16* (2013.01); *G01M 17/007* (2013.01)

(58) Field of Classification Search
CPC ..... G01N 17/04; G01N 17/043; G01N 17/02
USPC .......................... 702/33–35; 205/775.5, 776
See application file for complete search history.

(56) References Cited

U.S. PATENT DOCUMENTS

| | | | |
|---|---|---|---|
| 8,647,498 B2* | 2/2014 | Nakada ................ | G01N 17/043 204/404 |
| 9,109,989 B2* | 8/2015 | Hamann ................ | G01N 17/04 |

FOREIGN PATENT DOCUMENTS

| | | |
|---|---|---|
| JP | 2005134162 A | 5/2005 |
| JP | 2008-542544 A | 11/2008 |
| JP | 2009053205 A | 3/2009 |

OTHER PUBLICATIONS

Japanese Office Action dated Oct. 28, 2015.
Kasai et al.; Estimation Method of Anti-corrosion Performance of Automotive Vehicles'; vol. 43, No. 11, p. 51-57, Nov. 1989.

* cited by examiner

*Primary Examiner* — An Do
(74) *Attorney, Agent, or Firm* — Barnes & Thornburg LLP

(57) ABSTRACT

A mobile body corrosion measuring apparatus having a corrosion sensor installed in at least one portion of a mobile body, the corrosion sensor measuring a corrosion state at the portion and outputting corrosion data; a vehicle (mobile body) running speed sensor installed in the mobile body, the running speed sensor measuring a running speed of the mobile body and outputting the running speed data; and a data collection unit that acquires the corrosion data from the corrosion sensor and the running speed data from the vehicle speed sensor at the same time and collects the corrosion data and the running speed data with the corrosion data and the running speed data associated with each other. Due to above structure, a corrosion state specific to the mobile body can be accurately measured.

8 Claims, 10 Drawing Sheets

METHOD AND APPARATUS FOR MEASURING CORROSION OF MOBILE BODY

PRIORITY CLAIM

This patent application claims priority to Japanese Patent Application No. 2012-130534, filed 8 Jun. 2012, the disclosure of which is incorporated herein by reference in its entirety.

BACKGROUND OF THE INVENTION

1. Field of the Invention

The present invention relates to a method of measuring corrosion of a mobile body having an engine and apparatus for measuring a corrosion state (corrosion status) in at least one portion of the mobile body such as an automobile.

2. Description of the Related Art

The corrosion state of the automobile (mobile body having an engine) is greatly different depending on each portion thereof and thus a conventional corrosion test is performed in such a manner that the corrosion state is measured by attaching an exposed material made of a steel plate to the each portion thereof. Unfortunately, a long-term exposure is required for measuring the corrosion state using the exposed material, and thus it is extremely difficult to know a variation of the corrosion state as a time passes.

In view of this, as disclosed in Patent document 1 (Japanese Patent Laid-Open No. 2005-134162) and Patent document 2 (Japanese Patent Laid-Open No. 2009-53205), there has been proposed a method of quantitatively measuring a corrosion state as well as a temperature and a humidity at each portion of a vehicle by attaching, to the each portion of the vehicle, a corrosion sensor and a temperature/humidity sensor that have conventionally been used in a building structure such as a bridge and a building.

Meanwhile, a vehicle (mobile body) such as an automobile runs and stops, while a corrosion state at each position of the vehicle changes depending on a running state thereof. In other word, the corrosion state of each position of the vehicle is either significantly affected by vehicle running speed or not affected by vehicle running speed.

Thus, the corrosion state specific to such a vehicle different from a building structure cannot be accurately measured and known simply by installing such a corrosion sensor as disclosed above in Patent documents 1 and 2 in the vehicle.

SUMMARY OF THE INVENTION

The present invention has been made and achieved under such circumstances, and an object of the present invention is to provide a method and apparatus for measuring corrosion of a mobile body having an engine, that are capable of accurately measuring a corrosion state specific to a mobile body.

A mobile body corrosion measuring method according to the present invention comprises the steps of: measuring a corrosion state in at least one portion of the mobile body and outputting corrosion data by a corrosion sensor installed in the portion; measuring a running speed of the mobile body and outputting running speed data by a running speed sensor installed in the mobile body; and acquiring the corrosion data and the running speed data at a same timing and collecting the corrosion data and the running speed data with the corrosion data and the running speed data associated with each other by a data collection unit.

An apparatus for measuring corrosion of a mobile body having an engine according to the present invention comprises:

a corrosion sensor that is installed in at least one portion of the mobile body, the corrosion sensor measuring a corrosion state at the portion, and outputting corrosion data;

a running speed sensor that is installed in the mobile body, the running speed sensor measuring a running speed of the mobile body, and outputting running speed data; and a data collection unit that acquires the corrosion data from the corrosion sensor and the running speed data from the running speed sensor at a same timing and collects the corrosion data and the running speed data with the corrosion data and the running speed data associated with each other.

The method and apparatus for measuring corrosion of the mobile body according to the present invention allow the corrosion data from the corrosion sensor and the running speed data of the mobile body from the running speed sensor to be acquired at the same timing and to be collected with the corrosion data and the running speed data associated with each other, thus allowing a corrosion state specific to the mobile body to be accurately measured, with the corrosion state at a portion of the mobile body having a correlation with the running speed of the mobile body.

DESCRIPTION OF THE PREFERRED EMBODIMENT

Hereinafter, an embodiment of the present invention will be described with reference to the accompanying drawings.

Figure 1:
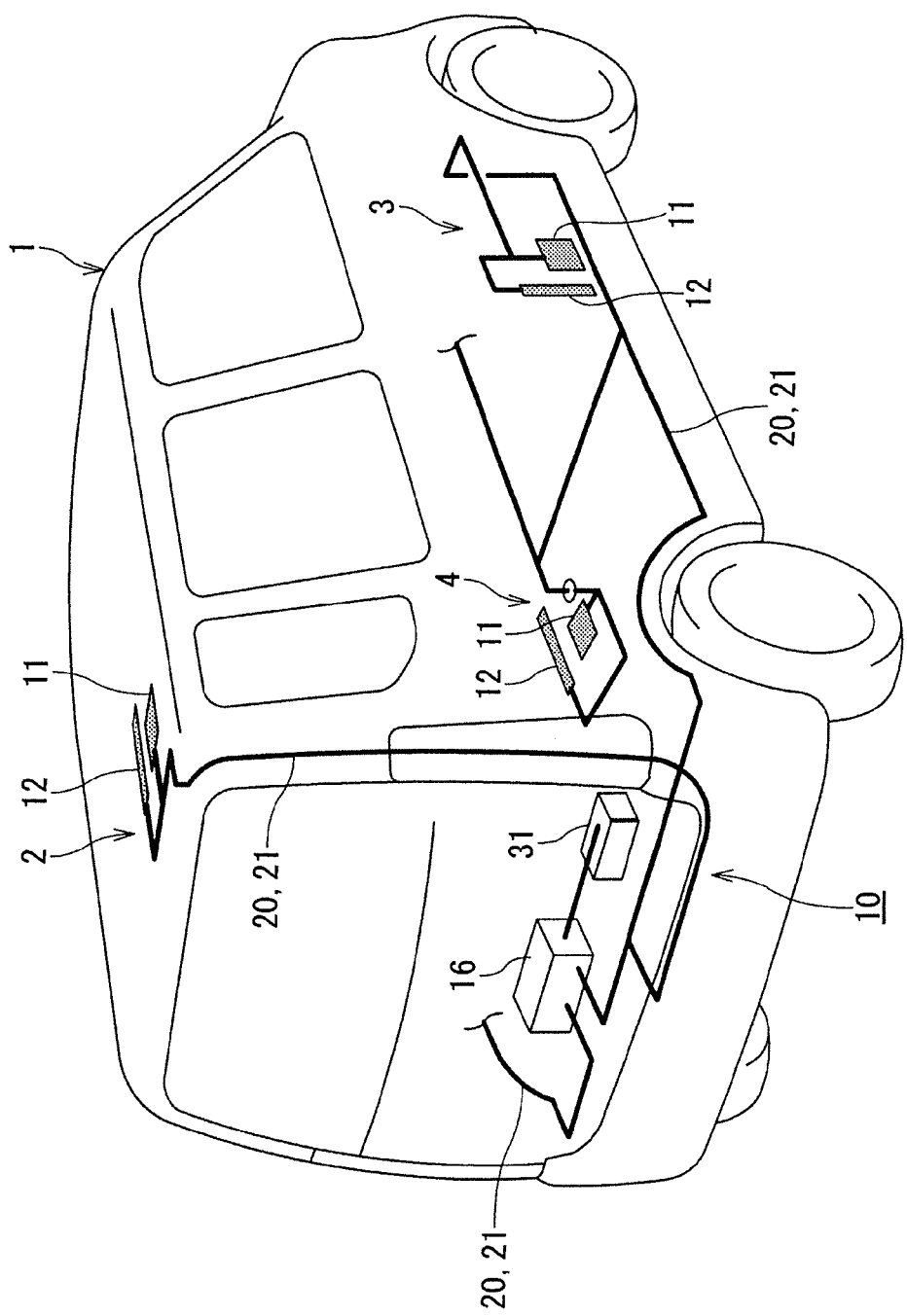
FIG. 1 is a perspective view illustrating an experimental vehicle as a corrosive environment measuring apparatus according to an embodiment of a mobile body corrosion measuring apparatus of the present invention.
Figure 2:
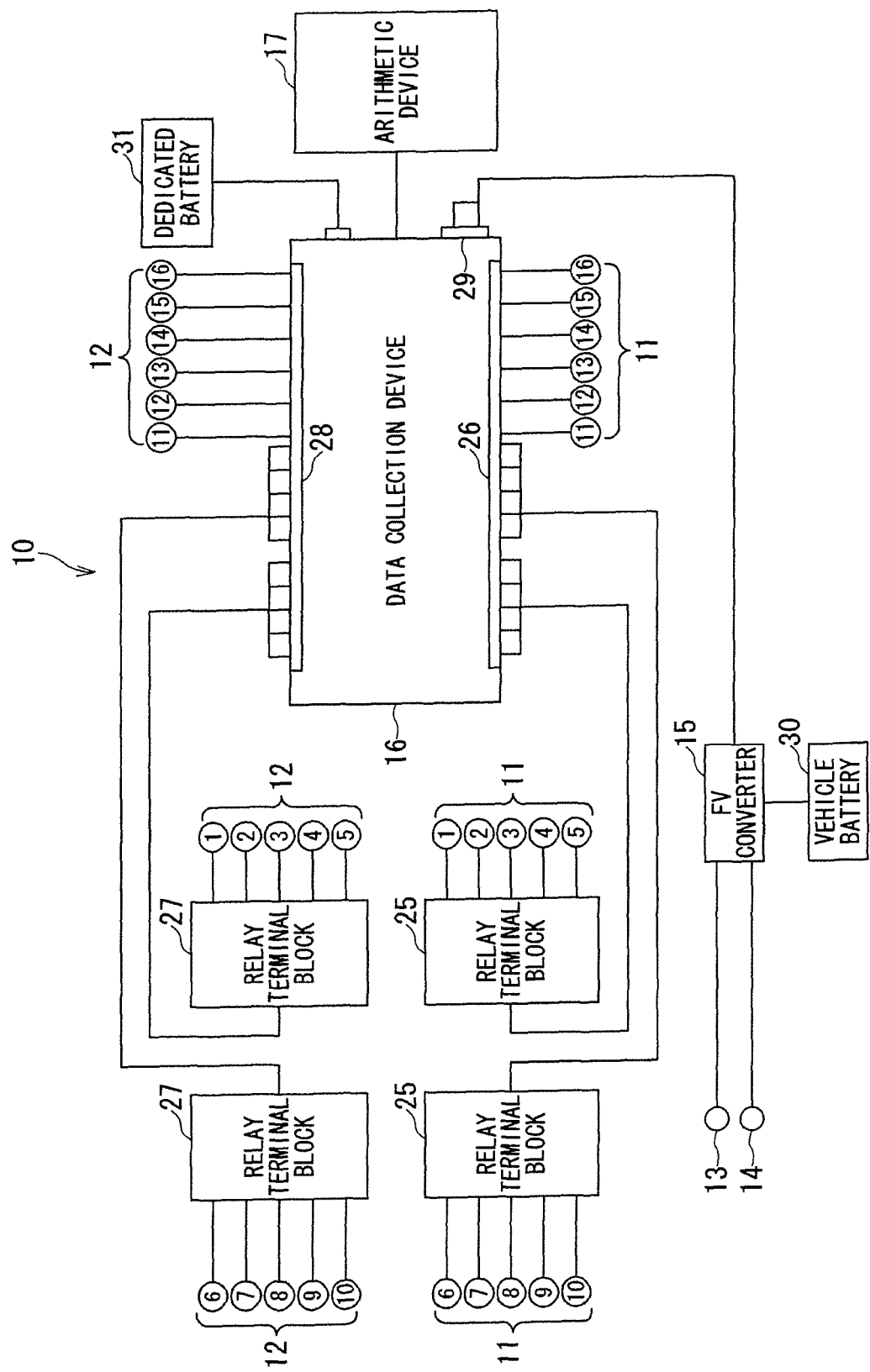
FIG. 2 is a block diagram illustrating a configuration of the corrosive environment measuring apparatus shown in FIG. 1.

FIG. 1 is a perspective view illustrating an experimental vehicle as a corrosive environment measuring apparatus according to an embodiment of a mobile body corrosion measuring apparatus of the present invention. FIG. 2 is a block diagram illustrating a configuration of the corrosive environment measuring apparatus of FIG. 1.

FIGS. 1 and 2 illustrate a corrosive environment measuring apparatus 10 as the mobile body corrosion measuring apparatus which measures a corrosion state and a corrosive environment (such as a temperature and a humidity) at a plurality of positions of the experimental vehicle (such as a four-wheeled vehicle) 1 as the mobile body by associating them with a speed (vehicle speed) of the experimental vehicle 1 and an engine rotation speed (number of revolution of engine) thereof. The corrosive environment measuring apparatus 10 includes a plurality of corrosion sensors 11, a plurality of temperature/humidity sensors 12 as environmental sensors, a vehicle running speed sensor 13 as a running speed sensor, an engine rotation speed sensor 14, an FV converter 15 as a signal processing unit, a data collection device 16 as a data collection unit, and an arithmetic device 17 as an arithmetic unit.

As illustrated in FIG. 1, each corrosion sensor 11 is installed in at least one portion of the experimental vehicle 1, namely, at each portion thereof such as a roof 2, a door interior 3, and a floor bottom surface 4. As described in detail later, the each corrosion sensor 11 measures a corrosion state at each portion thereof and outputs corrosion data. In addition, the temperature/humidity sensors 12 are installed in pairs with the corrosion sensors 11 in the vicinity of each corrosion sensor 11. Each temperature/humidity sensor 12 measures a temperature and a humidity around each corrosion sensor 11 as an environmental element, and outputs temperature/humidity data (temperature data and humidity data) as environmental data.

Figure 3A:
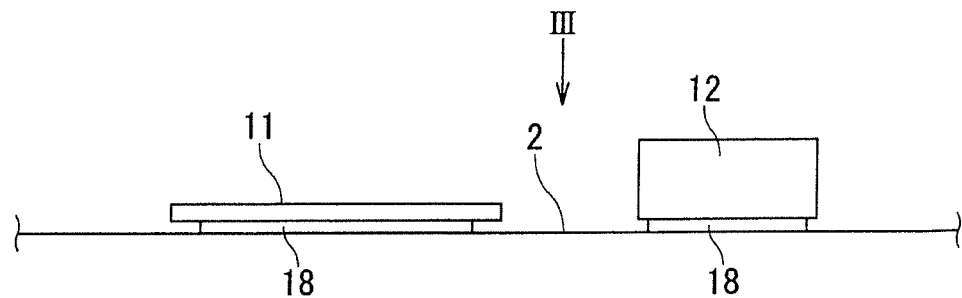
FIGS. 3A-3B illustrate an example of installation of a corrosion sensor and a temperature/humidity sensor in FIG. 1, with FIG. 3A a side view thereof and FIG. 3B a view along line III in FIG. 3A.
Figure 3B:
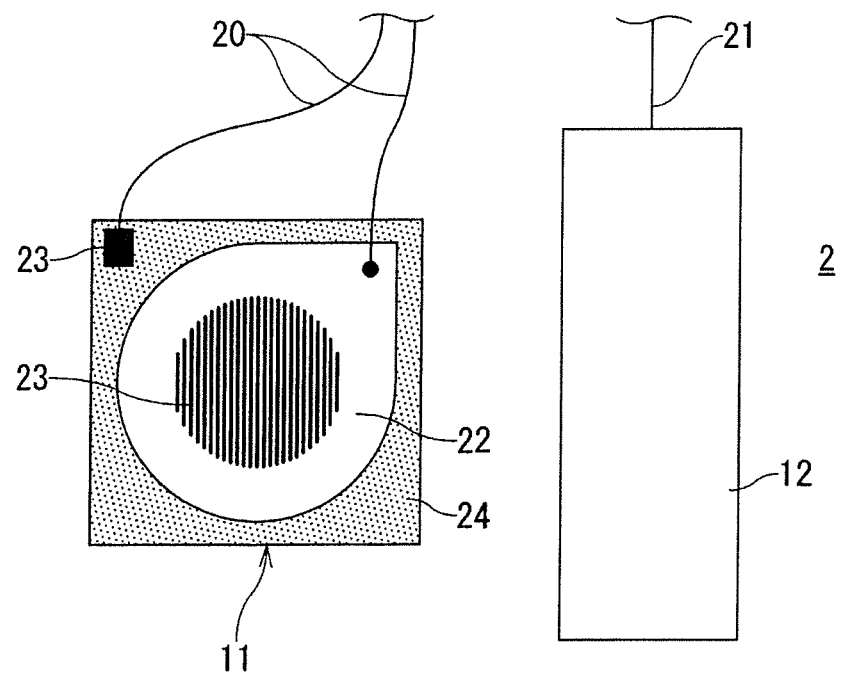

As illustrated in FIGS. 3A-B, the corrosion sensor 11 and the temperature/humidity sensor 12 are installed in such a manner that if the installed portions can secure flat portions like the roof 2 and the door interior 3, the sensors are directly adhered to the flat portions using a double-sided tape 18 or the like.

Figure 5A:
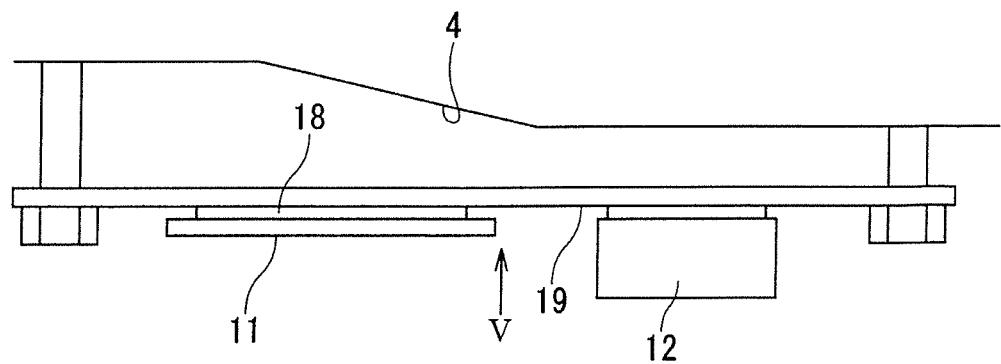
FIGS. 5A-B illustrate another example of installation of the corrosion sensor and the temperature/humidity sensor in FIG. 1, with FIG. 5A a side view thereof and FIG. 5B a view along line V in FIG. 5A.
Figure 5B:
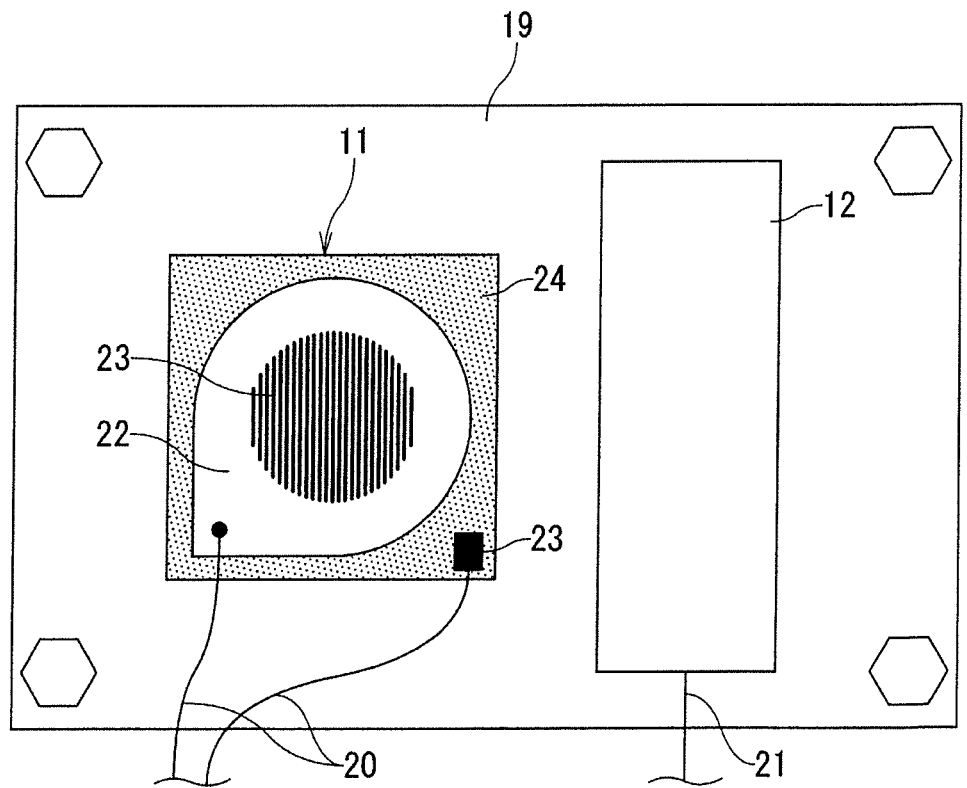

Alternatively, as illustrated in FIGS. 5A-B, the corrosion sensor 11 and the temperature/humidity sensor 12 are installed in such a manner that if the installed portions cannot secure the flat portions like the floor bottom surface 4, for example, a plastic plate 19 is attached to the floor bottom surface 4, and then the sensors are adhered to the plate 19 using a double-sided tape 18 or the like. Further, wirings 20 from the corrosion sensor 11 and a wiring 21 from the temperature/humidity sensor 12 pass through a vehicle compartment floor carpet and an interior cover inside the experimental vehicle 1 and are connected to a data collection device 16 with care not to be disconnected as illustrated in FIG. 1.

Figure 4:
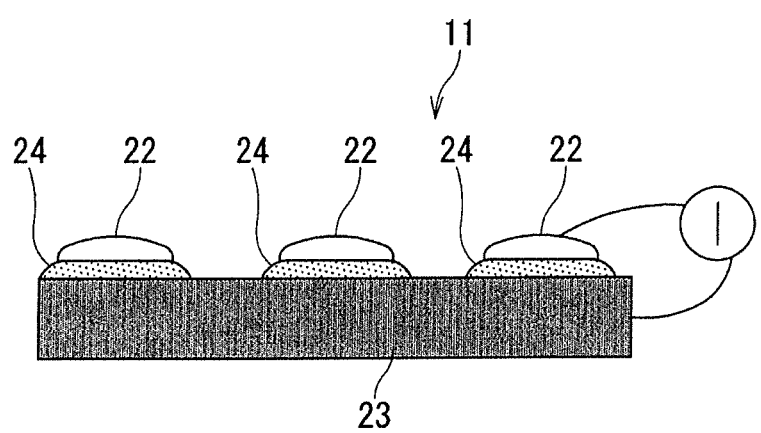
FIG. 4 is a sectional side view of the corrosion sensor illustrated in FIGS. 3A-B and 5A-B.

Here, as illustrated in FIGS. 3B, 4, and 5B, the corrosion sensor 11 is a galvanic type corrosion sensor such that a silver electrode 22 and an iron electrode 23 using a dissimilar metal (such as silver and iron) as an electrode thereof are configured with an insulating material 24 such as silicon dioxide disposed thereunder and measures a current (galvanic current) generated by a cell formed by the silver electrode 22 and the iron electrode 23 with a solution or a water membrane interposed therebetween.

An output (current value) of the corrosion sensor 11 is corrosion data acquired by directly measuring corrosion of the silver electrode 22 and the iron electrode 23, but indirectly indicates a corrosion state when corrosion occurs in a portion in which the corrosion sensor 11 is installed (that is an iron-made portion of the experimental vehicle 1). Specifically, corrosion proceeds at a portion once exposed to water splash or the like until the surface thereof is dry. In the same manner as the corrosion phenomenon of this portion, when the corrosion sensor 11 is wet, the output of the corrosion sensor 11 increases, and gradually decreases as the surface thereof becomes dry.

The vehicle running speed sensor 13 illustrated in FIG. 2 is installed in a predetermined position of the experimental vehicle 1. The vehicle speed sensor 13 continuously measures a running speed (vehicle speed) of the experimental vehicle 1 and outputs vehicle running speed data as running speed data to the FV converter 15. The engine rotation speed (engine rotation rate) sensor 14 is installed in an engine (unillustrated) of the experimental vehicle 1. The engine rotation speed sensor 14 continuously measures an engine rotation speed and outputs engine rotation speed data to the FV converter 15.

The vehicle running speed data from the vehicle running speed sensor 13 and the engine rotation speed data from the engine rotation speed sensor 14 are of pulse shape, and thus the FV converter 15 continuously inputs the pulse data from the vehicle running speed sensor 13 and the engine rotation speed sensor 14, continuously converts the pulse data to voltage data such as 0 to 1 volt, and outputs the voltage data to the data collection device 16.

During engine operation, the FV converter 15 connected to the vehicle running speed sensor 13 and the engine rotation speed sensor 14 converts the vehicle running speed data from the vehicle running speed sensor 13 and the engine rotation speed data from the engine rotation speed sensor 14 to voltage data. During engine stop, data conversion is not required, and thus power is supplied from a vehicle battery 30 commonly installed in the experimental vehicle 1. Note that this makes it possible to suppress power consumption of a later described dedicated battery 31.

The data collection device 16 includes input ports 26 having a plurality of channels (16 channels in the present embodiment) which input corrosion data from a plurality of (16 in the present embodiment) corrosion sensors 11 through relay terminal blocks 25. In addition, the data collection device 16 includes input ports 28 having a plurality of channels (16 channels for each temperature sensor and humidity sensor in the present embodiment) which input temperature/humidity data from a plurality of (16 in the present embodiment) temperature/humidity sensors 12 through relay terminal blocks 27. Further, the data collection device 16 includes input ports 29 having 2 channels which input vehicle running speed data and engine rotation speed data (both voltage data) from the FV converter 15.

The data collection device 16 acquires (samples) corrosion data from the corrosion sensors 11, temperature/humidity data from the temperature/humidity sensors 12, and vehicle running speed data and engine rotation speed data from the FV converter 15 at a same timing; and collects the corrosion data, the temperature/humidity data, the vehicle running speed data, and the engine rotation speed data acquired at the same timing and associated with each other. The corrosion data, the temperature/humidity data, the vehicle running speed data, and the engine rotation speed data are acquired, for example, at a time interval of about 10 minutes since the corrosion data and the temperature/humidity data slowly change.

Power is supplied to the data collection device 16 from the dedicated battery 31 different from the vehicle battery 30 of the experimental vehicle 1. The data collection device 16 needs to acquire the corrosion data from the corrosion sensors 11 and the temperature/humidity data from the temperature/humidity sensors 12 at the aforementioned time interval during the engine operation of the experimental vehicle 1 and the engine stop thereof. Thus, when power is supplied to the data collection device 16 from the vehicle battery 30, the vehicle battery 30 may be subject to power loss (dead battery). In order to avoid this problem, the dedicated battery 31 is installed.

When power is supplied to the data collection device 16 from the dedicated battery 31, the data collection device 16 acquires the corrosion data from the corrosion sensors 11, the temperature/humidity data from the temperature/humidity sensors 12, and the vehicle running speed data and the engine rotation speed data from the FV converter 15 and collects the data associated with each other. At this time, the longer the timing interval is, the more the power consumption of the dedicated battery 31 can be reduced. From this point of view, the timing interval at which the data collection device 16 acquires data is appropriately set to about 10 minutes.

Here, as illustrated in FIG. 1, the data collection device 16 is installed in, for example, a loading space of the experimental vehicle 1 together with the dedicated battery 31. The FV converter 15 may also be installed in the loading space of the experimental vehicle 1.

As described above, the data collection device 16 collects the corrosion data, the temperature/humidity data, the vehicle running speed data, and the engine rotation speed data acquired at the same timing and associated with each other. For example, as illustrated in FIGS. 6A-C, the correlation between the corrosion data (output of the corrosion sensors 11) and the vehicle running speed data (vehicle speed) can be measured.

Figure 6A:
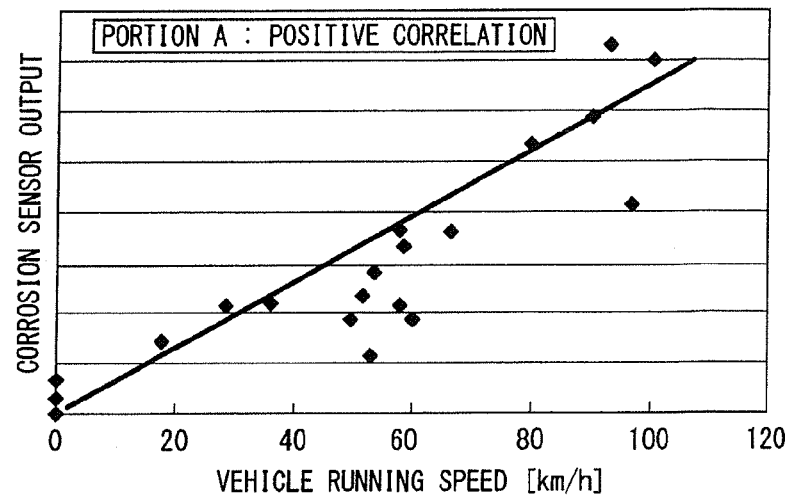
FIGS. 6A-C are graphs illustrating a relation between an output of the corrosion sensor of FIG. 1 and a vehicle speed for each portion of the vehicle.
Figure 6B:
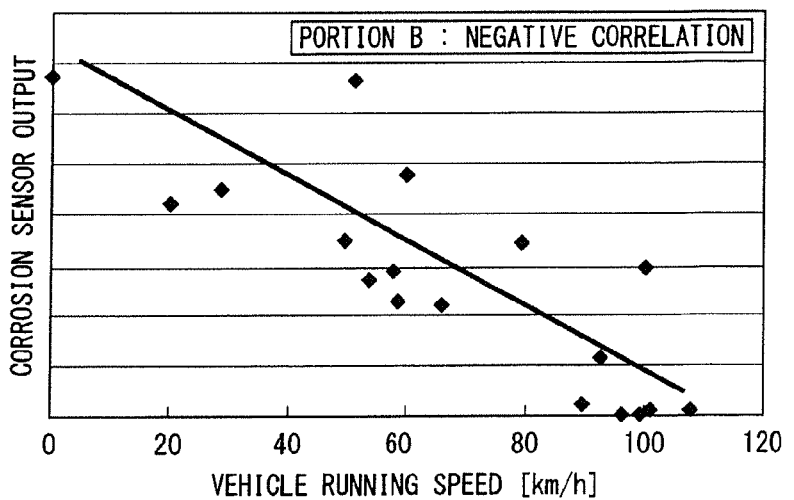
Figure 6C:
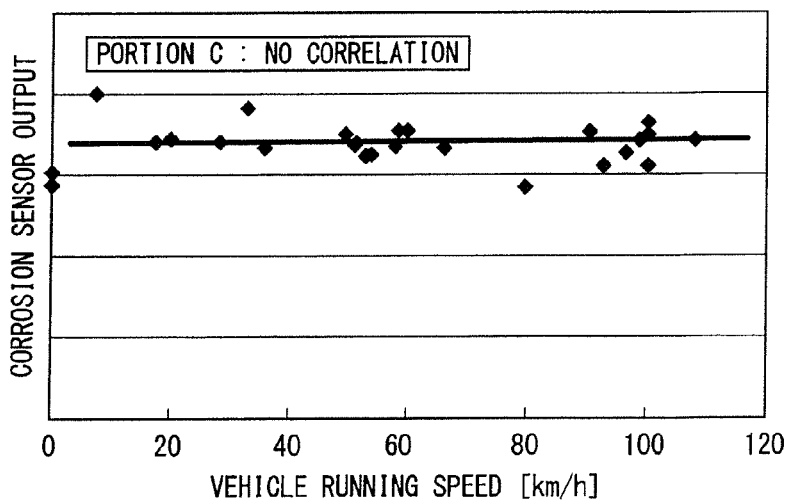

More specifically, as illustrated in FIG. 6A, the corrosion data increases at portion A of the experimental vehicle 1 as the vehicle running speed data increases. Thus, the corrosion data has a positive correlation with the vehicle running speed data. In addition, as illustrated in FIG. 6B, the corrosion data decreases at portion B of the experimental vehicle 1 as the vehicle running speed data increases. Thus, the corrosion data has a negative correlation with the vehicle speed data. Further, as illustrated in FIG. 6C, the corrosion data is not affected by the vehicle running speed data at portion C of the experimental vehicle 1. Thus, the corrosion data has no correlation with the vehicle running speed data. Note that the measurement results illustrated in FIGS. 6A-C were acquired when the experimental vehicle 1 traveled and run in a snow-covered area during snowfall.

Meanwhile, there is a problem in that if the data collection device 16 acquires the vehicle running speed data at the same time when the experimental vehicle 1 accidentally stops at a signal or the like while driving, the correlation between the corrosion data (output of the corrosion sensor 11) and the vehicle running speed data (vehicle speed) acquired at the same timing differs. For example, the corrosion data has a positive correlation with the vehicle s running speed data at a portion exposed to water splash. At this time, if the data collection device 16 acquires the vehicle running speed data at the same time when the experimental vehicle 1 temporarily stops, the corrosion sensor 11 outputs a large current value since the experimental vehicle 1 stops immediately after it is exposed to water splash, but the vehicle speed sensor 13 outputs the vehicle speed data indicating that the vehicle speed is 0. As a result, the corrosion data has a negative correlation with the vehicle speed data.

In order to solve such problems, the present embodiment executes any one of a first solution unit and a second solution unit. First, even if the vehicle running speed data measured by the vehicle running speed sensor 13 is 0 km/h, the first solution unit uses the engine rotation speed data measured by the engine rotation speed sensor 14 so as to determine whether the experimental vehicle 1 temporarily stops by chance while driving or the engine stops and the experimental vehicle 1 completely stops so as to select data acquired and collected by the data collection device 16. The selection is executed by the arithmetic unit 17 (FIG. 2) installed in the data collection device 16.

Specifically, the arithmetic device 17 is configured as follows. Namely, among the engine rotation speed data, the vehicle running speed data, the corrosion data, and the temperature/humidity data fetched from the data collection device 16, the data associated with the case in which the engine rotation speed data is greater than 0 rpm and the vehicle running speed data is 0 km/h is deleted and at least the corrosion data, the temperature/humidity data, and the vehicle running speed data associated with the other cases are kept in the arithmetic device 17.

Figure 7:
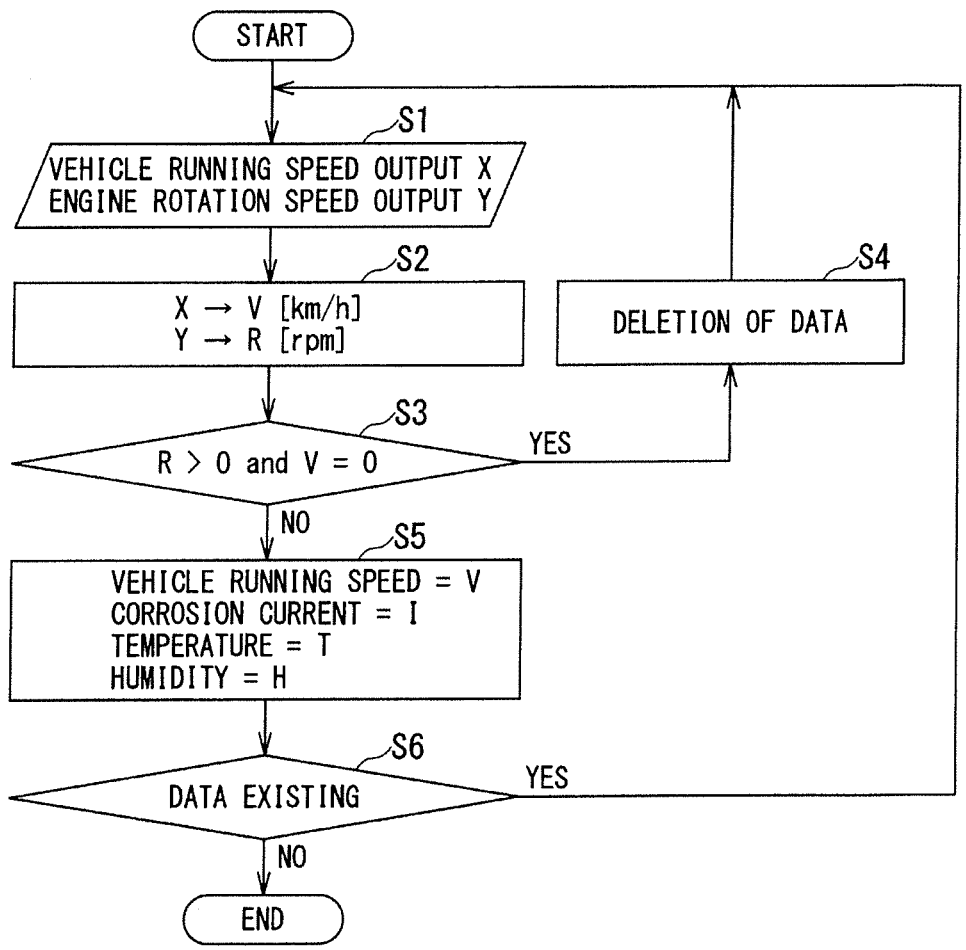
FIG. 7 is a flowchart illustrating a procedure for selecting data collected by a data collection device of FIG. 1.

Specifically, as illustrated in FIG. 7, the vehicle running speed data (vehicle running speed output X) outputted from the vehicle running speed sensor 13 and the engine rotation speed data (engine rotation speed output Y) outputted from the engine rotation speed sensor 14 are converted to voltage values by the FV converter 15, namely, the vehicle running speed V (km/h) and the engine rotation speed R (rpm) respectively, which are acquired by the data collection device 16 and confirmed by the arithmetic device 17 (S1 and S2).

Among the corrosion data, the temperature/humidity data, the vehicle running speed data (vehicle speed V), and the engine rotation speed data (engine rotation speed R) associated and collected by the data collection device 16, the arithmetic device 17 determines whether the engine rotation speed R is greater than 0 rpm (R>0) and the vehicle running speed V is 0 km/h (V=0) or not (S3). If a determination is made in step S3 that R>0 and V=0, the arithmetic device 17 deletes the corrosion data and the temperature/humidity data associated with the vehicle running speed data and the engine rotation speed data including the vehicle running speed data and the engine rotation speed data (S4).

In step S3, if the arithmetic device 17 determines that the engine rotation speed R is greater than 0 rpm and the vehicle running speed V is not 0 km/h; or the engine rotation speed R is 0 rpm and the vehicle running speed V is 0 km/h, the corrosion data (corrosion current I), the temperature/humidity data (temperature T and humidity H), and the vehicle running speed data (vehicle running speed V) associated with each of the cases and with each other are kept in the arithmetic device 17 (S5). The data kept in the arithmetic device 17 is such that the corrosion data particularly has an accurate correlation with the vehicle running speed data.

The arithmetic device 17 determines whether other data (associated and collected corrosion data, temperature/humidity data, vehicle running speed data, or engine rotation speed data) fetched from the data collection device 16 exists or not (S6). If data exists, the arithmetic device 17 executes steps S1 to S6 on all the remaining data.

If the FV converter 15 has a function for outputting the vehicle running speed data inputted from the vehicle running speed sensor 13 as time-averaged data, the second solution unit uses this function such that the data collection device 16 acquires the average vehicle running speed data (average running speed data) from the FV converter 15 as the vehicle running speed data at the same timing as the corrosion data from the corrosion sensors 11 and the temperature/humidity data from the temperature/humidity sensors 12, and collects the vehicle running speed data (average vehicle running speed data), the corrosion data, and the temperature/humidity data acquired at the same timing and associated with each other.

Here, the average vehicle running speed data is a value calculated by averaging the vehicle running speed data from the vehicle running speed sensor 13 at a predetermined time interval (preferably 0.5 to 2 minute interval as described later) shorter than an acquisition time interval (for example, a 10-minute interval) in which the data collection device 16 acquires the corrosion data from the corrosion sensors 11 and the temperature/humidity data from the temperature/humidity sensors 12.

Figure 8:
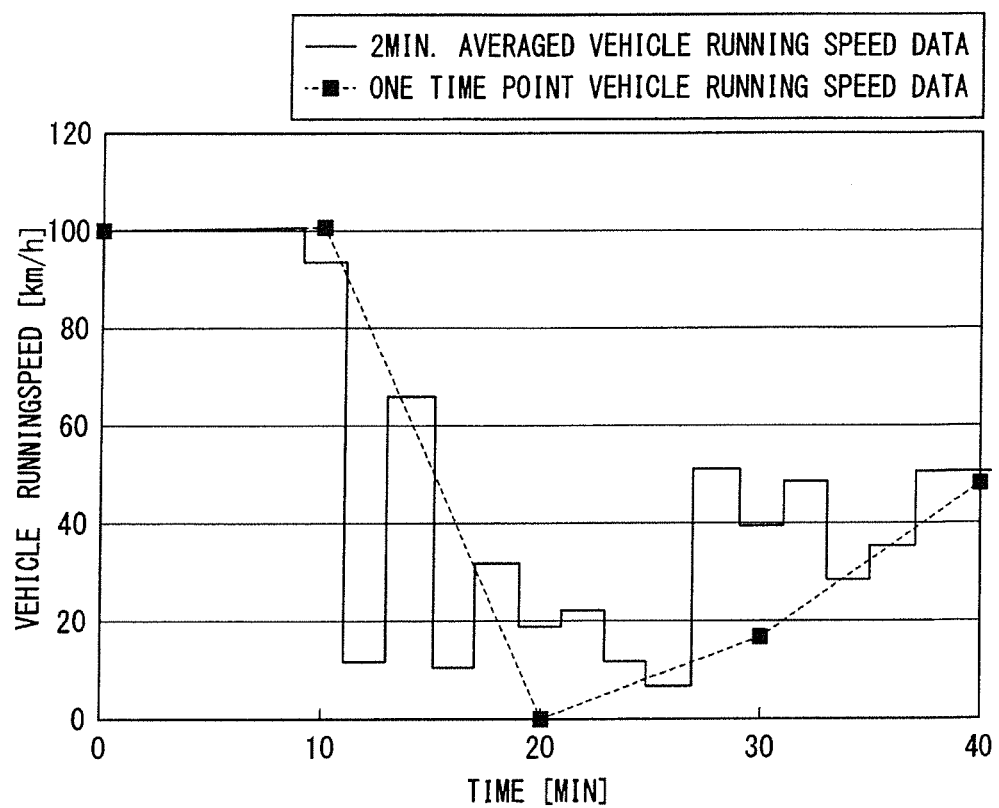
FIG. 8 is a graph comparing vehicle speed data at one point of time with average vehicle speed data for every two minutes.

FIG. 8 is a graph illustrating a difference between one-time vehicle running speed data measuring the vehicle running speed data from the vehicle running speed sensor 13 once every 10 minutes and 2-minute average vehicle running speed data calculated by averaging the vehicle running speed data from the vehicle running speed sensor 13 once every two minutes.

For example, at a time point of 20 minutes, the one-time vehicle running speed data is 0 km/h, and the 2-minute average vehicle running speed data is about 20 km/h, from which it is understood that one-time vehicle running speed data is a value measuring the vehicle running speed when the experimental vehicle 1 temporarily stops by chance.

In addition, at a time point of 30 minutes, the one-time vehicle running speed data is about 20 km/h, and the 2-minute average vehicle running speed data is 40 km/h, from which it is understood that one-time vehicle running speed data is a value measuring the vehicle running speed when the experimental vehicle 1 is decelerating.

Figure 9:
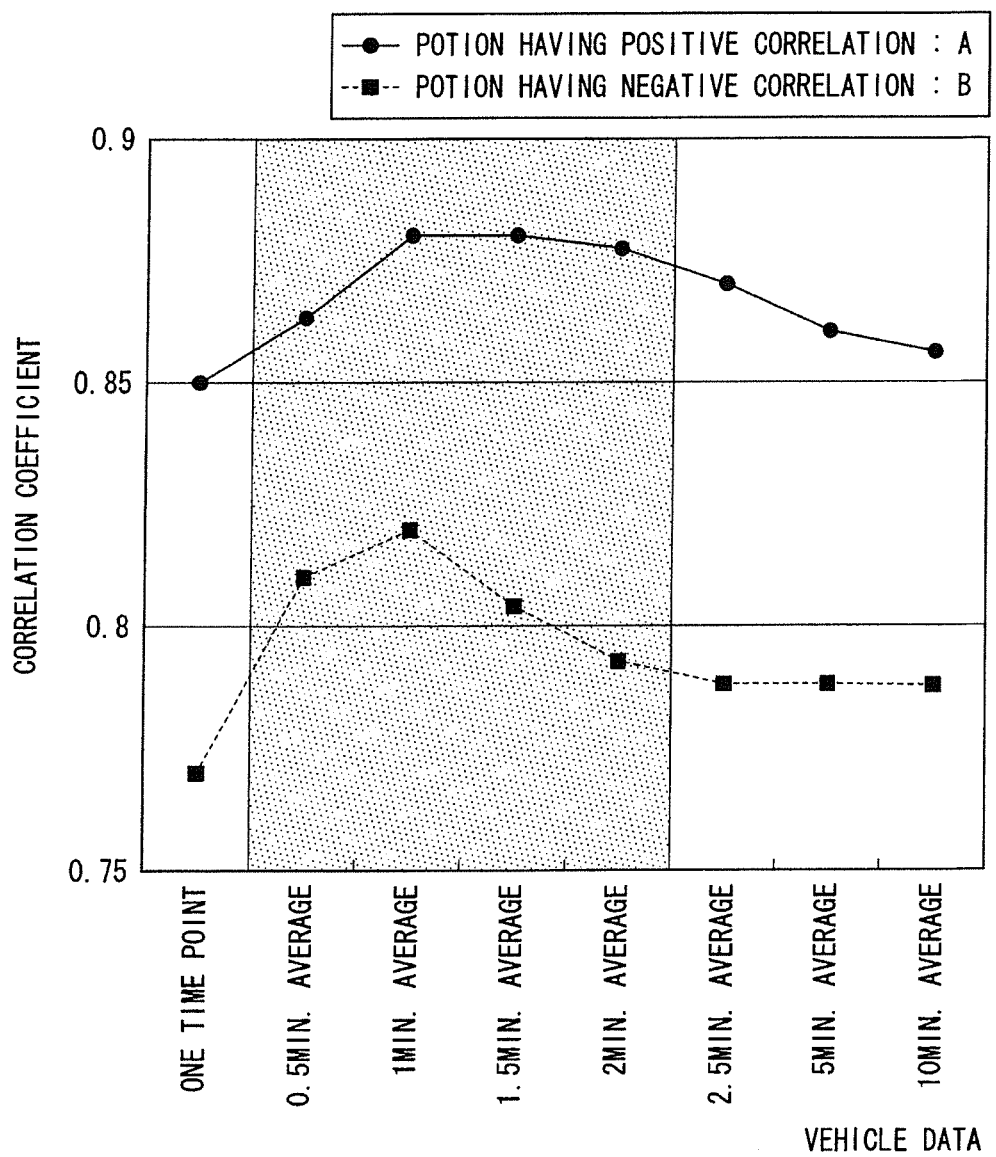
FIG. 9 is a graph illustrating a relation between a correlation coefficient indicating a correlation between an output of the corrosion sensor and a vehicle speed and a vehicle speed different in acquisition (sampling) method at portions having the correlation.
Figure 10:
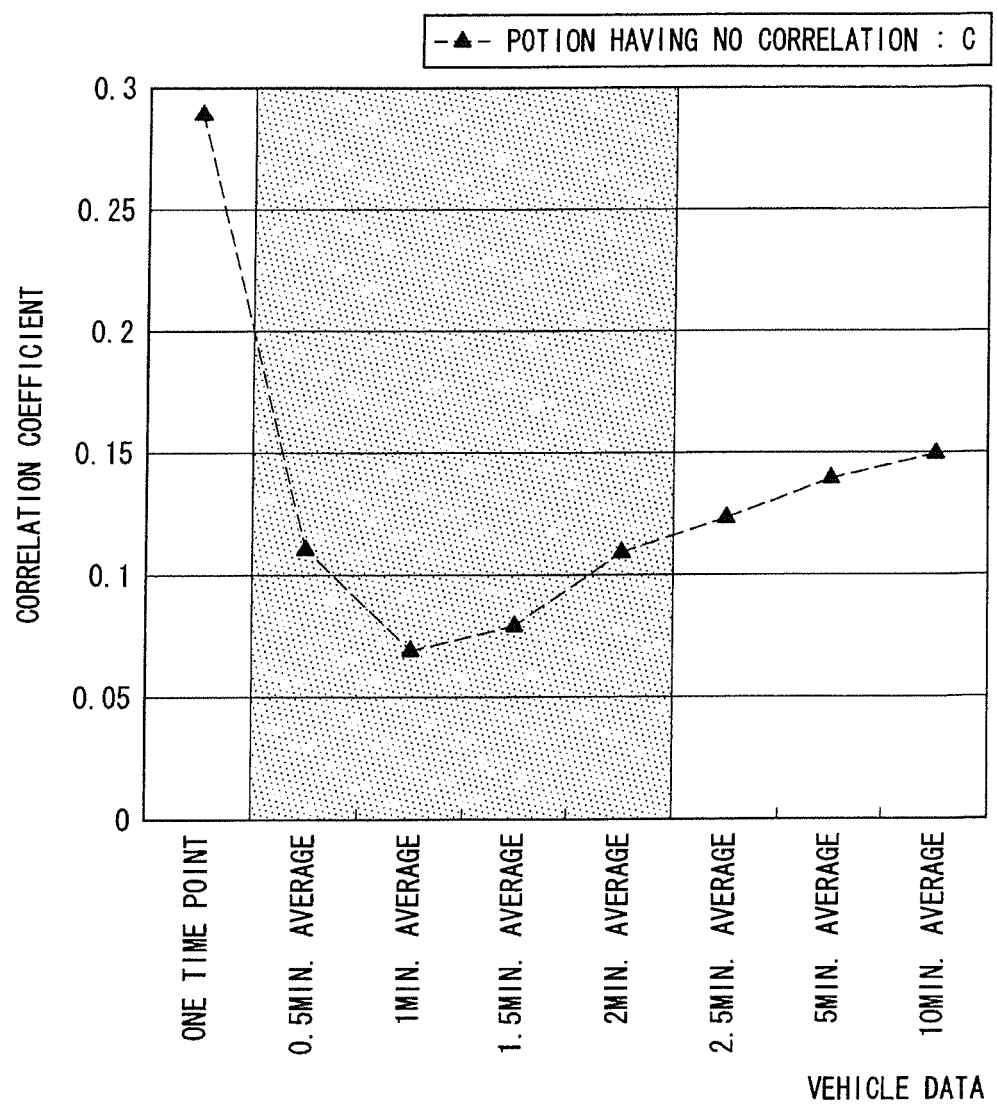
FIG. 10 is a graph illustrating a relation between a correlation coefficient indicating a correlation between an output of the corrosion sensor and a vehicle speed and a vehicle speed different in acquisition (sampling) method at a portion not having the correlation.

In a first case and a second case regarding the data acquisition as described below, FIG. 9 is a graph illustrating a relation between a correlation coefficient indicating a correlation between the corrosion data from the corrosion sensors 11 and the vehicle running speed data and the vehicle running speed data different in acquisition method at portion A (portion where the corrosion data has a positive correlation with the vehicle running speed data) of the experimental vehicle 1 and at portion B (portion where the corrosion data has a negative correlation with the vehicle running speed data); and FIG. 10 is a graph illustrating the relation at portion C (portion where the corrosion data has no correlation with the vehicle running speed data) of the experimental vehicle 1.

Here, in the first case, the data collection device 16 acquires the corrosion data from the corrosion sensors 11, the temperature/humidity data from the temperature/humidity sensors 12, and the vehicle running speed data not averaged by the FV converter 15 from the vehicle running speed sensor 13 once every about 10 minutes at the same timing.

In the second case, the data collection device 16 acquires the average vehicle running speed data as the vehicle running speed data calculated by averaging the vehicle running speed data from the vehicle running speed sensor 13 every 0.5 minutes, every 1 minute, every 1.5 minutes, every 2 minutes, every 2.5 minutes, every 5 minutes, and every 10 minutes by the FV converter 15 together with the corrosion data from the corrosion sensors 11, and the temperature/humidity data from the temperature/humidity sensors 12 once every about 10 minutes at the same timing.

As illustrated in FIG. 9, at portion A having a positive correlation and at portion B having a negative correlation, in the range of 0.5- to 2-minute average vehicle running speed data, the correlation coefficient is close to "1", indicating a high correlation between the corrosion data and the vehicle running speed data.

As illustrated in FIG. 10, at portion C having no correlation, in the range of 0.5- to 2-minute average vehicle running speed data, the correlation coefficient is close to "0", indicating a low correlation between the corrosion data and the vehicle running speed data.

From the above facts, the FV converter 15 is set to calculate by averaging the vehicle running speed data every 0.5 to 2 minutes and output the average vehicle running speed data to the data collection device 16, thereby allowing the data collection device 16 to acquire and collect data having an accurate correlation between the corrosion data and the vehicle running speed data.

The present embodiment configured as described above can exert and exhibit the following effects (1) to (4).

(1) A corrosion sensor 11 installed in each portion of the experimental vehicle 1 measures a corrosion state of the each portion and outputs corrosion data; a temperature/humidity sensor 12 installed in the vicinity of the corrosion sensor 11 measures a temperature and a humidity around the corrosion sensor 11 and outputs temperature/humidity data; a vehicle running speed sensor 13 installed in the experimental vehicle 1 measures a vehicle running speed of the experimental vehicle 1 and outputs vehicle running speed data; and a data collection device 16 acquires the corrosion data from the corrosion sensor 11, the temperature/humidity data from the temperature/humidity sensor 12, and the vehicle running speed data from the vehicle running speed sensor 13 through an FV converter 15 at the same timing and collects the corrosion data, the temperature/humidity data, and the vehicle running speed data acquired at the same timing and associated with each other.

This makes it possible to accurately measure a corrosion state specific to a mobile body including the experimental vehicle 1, in which particularly the corrosion state of each portion of the experimental vehicle 1 has a correlation with the vehicle running speed of the experimental vehicle 1. Based on the thus acquired data, anti-rust materials and surface treatments can be applied to and anti-rust structures can be adopted in portions under severe corrosion conditions in a mobile body including a vehicle.

In addition, the data (corrosion data, temperature/humidity data, vehicle running speed data, and presence or absence of sea salt particles and a snow melting material) acquired in each region of the world in the above described manner can be used to perform an anti-rust test (corrosion test) to meet the local circumstances using the vehicle speed as one of the test conditions.

(2) The data collection device 16 acquires the corrosion data from the corrosion sensors 11, the temperature/humidity data from the temperature/humidity sensors 12, the vehicle running speed data from the vehicle speed sensor 13 through the FV converter 15, and the engine rotation speed data from the engine rotation speed sensor 14 through the FV converter 15 at the same timing and associated with each other. Then, the arithmetic device 17 deletes the data associated with a case in which the engine rotation speed data is greater than 0 rpm and the vehicle running speed data is 0 km/h (that is the experimental vehicle 1 temporarily stops by chance while driving) from the corrosion data, the temperature/humidity data, the vehicle running speed data, and the engine rotation speed data associated and collected by the data collection device 16; and keeps at least the corrosion data, the temperature/humidity data, and the vehicle running speed data in the other cases in the arithmetic device 17. As a result, at least the corrosion data, the temperature/humidity data, and the vehicle running speed data kept in the arithmetic device 17 have an accurate correlation between particularly the corrosion data and the vehicle running speed data.

(3) The FV converter 15 averages the vehicle running speed data from the vehicle running speed sensor 13 at a predetermined time interval (a 0.5- to 2-minute interval) shorter than an acquisition time interval in which the data collection device 16 acquires the corrosion data and the temperature/humidity data to calculate the average vehicle running speed data (0.5- to 2-minute average vehicle running speed data).

Then, the data collection device 16 acquires the average vehicle running speed data from the FV converter 15 as the vehicle running speed data at the same timing, for example, about every 10 minutes as the corrosion data from the corrosion sensors 11 and the temperature/humidity data from the temperature/humidity sensors 12 and collects the data associated with each other. Thus, in also this case, of the corrosion data, the temperature/humidity data, and the vehicle running speed data (average vehicle running speed data) collected by the data collection device 16, the correlation between the corrosion data and the vehicle running speed data can be made accurate.

(4) The data collection device 16 acquiring and collecting each data from the corrosion sensors 11, the temperature/humidity sensors 12, the vehicle running speed sensor 13, and the engine rotation speed sensor 14 is powered not by the vehicle battery 30 commonly installed in the experimental vehicle 1, but by the dedicated battery 31. Even during engine stop of the experimental vehicle 1, the data collection device 16 acquires and collects the corrosion data and the temperature/humidity data from the corrosion sensors 11 and the temperature/humidity sensors 12 respectively. Since power is supplied from the dedicated battery 31, the vehicle battery 30 can be prevented from power loss (dead battery).

So far, the present invention has been described based on the above embodiment thereof, but the present invention is not limited to the embodiment, and various modifications can be made without departing from the spirit and scope of the present invention.

For example, the corrosion sensor 11 is not limited to a galvanic type corrosion sensor, but may be a quartz crystal microbalance (QCM) or an impedance type corrosion sensor. In addition, the mobile body is not limited to a four-wheeled vehicle, but may be also a motorcycle, a ship, an outboard engine or an aircraft.

What is claimed is:

1. A method of measuring corrosion of a mobile body having an engine, the method comprising:
measuring a corrosion state in at least one portion of the mobile body and outputting corrosion data by a corrosion sensor installed in the portion;
measuring a running speed of the mobile body and outputting running speed data by a running speed sensor installed in the mobile body;
acquiring the corrosion data and the running speed data at a same timing and collecting the corrosion data and the running speed data with the corrosion data and the running speed data associated with each other;
measuring an engine rotation speed of the mobile body and outputting engine rotation speed data by an engine rotation speed sensor;
acquiring the engine rotation speed data at a same timing as the running speed data and the corrosion data, and collecting the engine rotation speed data with the running speed data, and the corrosion data associated with each other; and
deleting, from the engine rotation speed data, the running speed data, and the corrosion data collected with the engine rotation speed data, the running speed data, and the corrosion data associated with each other, data in a case in which the engine rotation speed data is greater than 0 and the running speed data is 0, and maintaining at least the corrosion data and the running speed data in other cases with the corrosion data and the running speed data associated with each other.

2. The method of measuring corrosion of the mobile body according to claim 1, further comprising:
measuring an environmental element such as a temperature and a humidity around the corrosion sensor and outputting environmental data by an environmental sensor installed in a vicinity of the corrosion sensor; and
acquiring the environmental data at a same timing as the corrosion data and the running speed data, and collecting the environmental data with the environmental data, the corrosion data, and the running speed data associated with each other.

3. A method of measuring corrosion of a mobile body having an engine, the method comprising:
measuring a corrosion state in at least one portion of the mobile body and outputting corrosion data by a corrosion sensor installed in the portion;
measuring a running speed of the mobile body and outputting running speed data by a running speed sensor installed in the mobile body;
acquiring the corrosion data and the running speed data at a same timing and collecting the corrosion data and the running speed data with the corrosion data and the running speed data associated with each other;
averaging the running speed data over a predetermined time interval shorter than an acquisition time interval at which a data collection unit acquires the corrosion data to calculate an average running speed data; and
acquiring the average running speed data as running speed data at a same timing as the corrosion data and collecting the average running speed data with the average running speed data and the corrosion data associated with each other.

4. The method of claim 3, further comprising:
measuring an environmental element such as a temperature and a humidity around the corrosion sensor and outputting environmental data by an environmental sensor installed in a vicinity of the corrosion sensor; and
acquiring the environmental data at a same timing as the corrosion data and the running speed data, and collecting the environmental data with the environmental data, the corrosion data, and the running speed data associated with each other.

5. An apparatus for measuring corrosion of a mobile body having an engine, the apparatus comprising:
a corrosion sensor that is installed in at least one portion of a mobile body, the corrosion sensor measuring a corrosion state at the portion, and outputting corrosion data;
a running speed sensor that is installed in the mobile body, the speed sensor measuring a running speed of the mobile body, and outputting running speed data;

a data collection unit that acquires the corrosion data from the corrosion sensor and the running speed data from the running speed sensor at a same timing and collects the corrosion data and the running speed data with the corrosion data and the running speed data associated with each other;

an engine rotation speed sensor that is installed in the mobile body, the engine rotation speed sensor measuring an engine rotation speed and outputting engine rotation speed data, wherein the data collection unit acquires the engine rotation speed data from the engine rotation speed sensor at a same timing as the running speed data from the running speed sensor and the corrosion data from the corrosion sensor and collects the engine rotation speed data with the engine rotation speed data, the running speed data, and the corrosion data associated with each other; and an arithmetic unit connected to the data collection unit is configured to delete data in a case in which the engine rotation speed data is greater than 0 and the speed data is 0 from the engine rotation speed data, the running speed data, and the corrosion data collected by the data collection unit with the engine rotation speed data, the running speed data, and the corrosion data associated with each other; and maintain at least the corrosion data and the running speed data in other cases with the corrosion data and the running speed data associated with each other.

6. The apparatus for measuring corrosion of the mobile body having the engine according to claim 5, further comprising:

an environmental sensor that is installed in a vicinity of the corrosion sensor, the environmental sensor measuring an environmental element such as a temperature and a humidity around the corrosion sensor and outputting environmental data, wherein the data collection unit acquires the environmental data from the environmental sensor at a same timing as the corrosion data from the corrosion sensor and the running speed data from the running speed sensor and collects the environmental data with the environmental data, the corrosion data, and the running speed data associated with each other.

7. An apparatus for measuring corrosion of a mobile body having an engine, the apparatus comprising:

a corrosion sensor that is installed in at least one portion of a mobile body, the corrosion sensor measuring a corrosion state at the portion, and outputting corrosion data;

a running speed sensor that is installed in the mobile body, the speed sensor measuring a running speed of the mobile body, and outputting running speed data;

a data collection unit that acquires the corrosion data from the corrosion sensor and the running speed data from the running speed sensor at a same timing and collects the corrosion data and the running speed data with the corrosion data and the running speed data associated with each other; and a signal processing unit connected to the running speed sensor averages the running speed data from the running speed sensor over a predetermined time interval shorter than an acquisition time interval at which the data collection device acquires the corrosion data to calculate average running speed data, the data collection unit acquires the average running speed data from the signal processing unit as running speed data at a same timing as the corrosion data from the corrosion sensor and collects the average running speed data with the average running speed data and the corrosion data associated with each other.

8. The apparatus for measuring corrosion of the mobile body having the engine according to claim 7, further comprising:

an environmental sensor that is installed in a vicinity of the corrosion sensor, the environmental sensor measuring an environmental element such as a temperature and a humidity around the corrosion sensor and outputting environmental data, wherein the data collection unit acquires the environmental data from the environmental sensor at a same timing as the corrosion data from the corrosion sensor and the running speed data from the running speed sensor and collects the environmental data with the environmental data, the corrosion data, and the running speed data associated with each other.

* * * * *